(12) United States Patent
Page et al.

(10) Patent No.: US 6,666,905 B2
(45) Date of Patent: Dec. 23, 2003

(54) THERMOELECTRIC PARTICLE PRECIPITATOR AND METHOD USING SAME FOR COLLECTING PARTICLES FROM FLUID STREAMS

(75) Inventors: Andrew E. Page, Kansas City, MO (US); Plamen G. Doynov, Kansas City, MO (US); Mary Ann Grelinger, Kansas City, KS (US); Chatten Cowherd, Jr., Lake Lotawana, MO (US); Timothy J. Sheeran, Herndon, VA (US)

(73) Assignee: Midwest Research Institute, Kansas City, MO (US)

( * ) Notice: Subject to any disclaimer, the term of this patent is extended or adjusted under 35 U.S.C. 154(b) by 17 days.

(21) Appl. No.: 09/844,384

(22) Filed: Apr. 27, 2001

(65) Prior Publication Data

US 2002/0014158 A1 Feb. 7, 2002

(51) Int. Cl.⁷ .................................................. B01D 5/00
(52) U.S. Cl. ................... 95/1; 95/8; 95/14; 95/289; 96/221; 62/3.2
(58) Field of Search ................... 95/289, 1, 8, 14; 96/221; 62/3.2, 3.4

(56) References Cited

U.S. PATENT DOCUMENTS

| | | | |
|---|---|---|---|
| 2,258,594 A | 10/1941 | Brewer et al. ............... 183/115 |
| 2,701,467 A | 2/1955 | Strong et al. .................... 73/28 |
| 2,839,155 A | 6/1958 | Martin .......................... 183/32 |
| 2,947,382 A | 8/1960 | Orr, Jr. .......................... 183/32 |
| 3,230,693 A | 1/1966 | Maecker et al. |
| 3,458,974 A | 8/1969 | Orr, Jr. et al. |
| 4,572,007 A | 2/1986 | Postma ..................... 73/863.12 |
| 4,675,031 A | 6/1987 | Sinnar |
| 4,832,715 A | 5/1989 | Naruse |

FOREIGN PATENT DOCUMENTS

| DE | 3936977 A1 | * | 5/1991 | .................... 62/3.4 |

* cited by examiner

Primary Examiner—Robert A. Hopkins
(74) Attorney, Agent, or Firm—Shook, Hardy & Bacon L.L.P.

(57) ABSTRACT

A thermoelectric particle precipitator for removing and collecting particles from a fluid stream. The thermoelectric particle precipitator utilizes one or more thermoelectric modules to create a temperature gradient which causes suspended particles in a fluid stream to undergo thermophoretic movement and precipitate on a surface on the cooled side of the temperature gradient. The collection surface may be a cooled surface of the thermoelectric module or a cooled surface of a thermal mass. The collected particles may be analyzed to determine their composition.

70 Claims, 5 Drawing Sheets

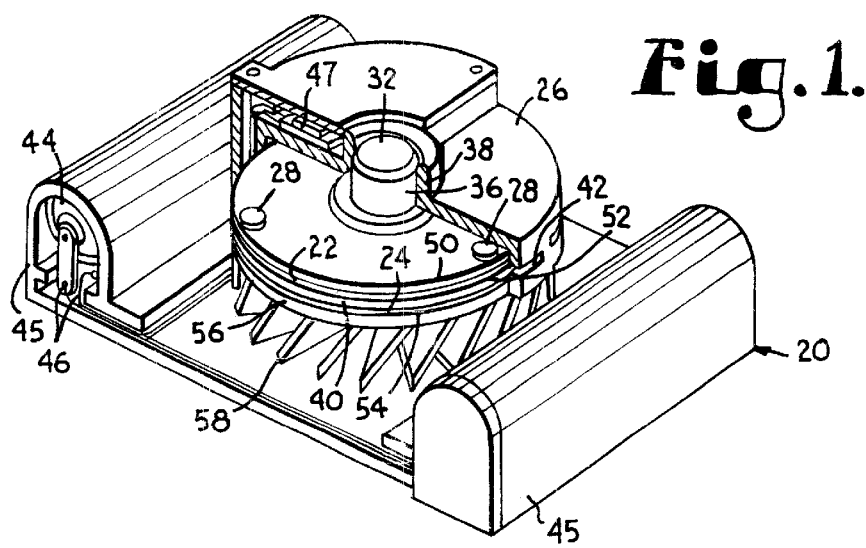
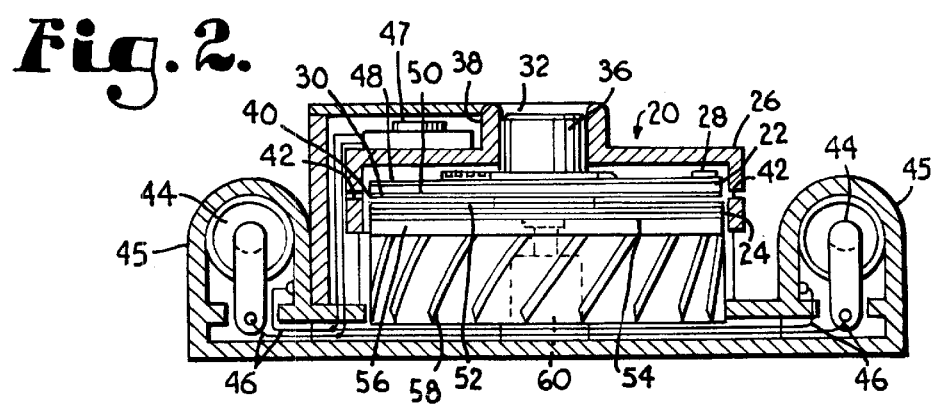
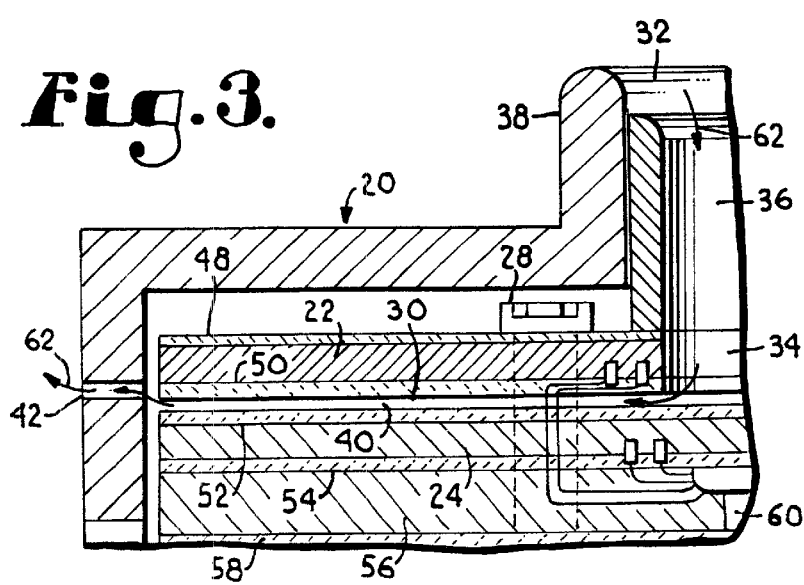

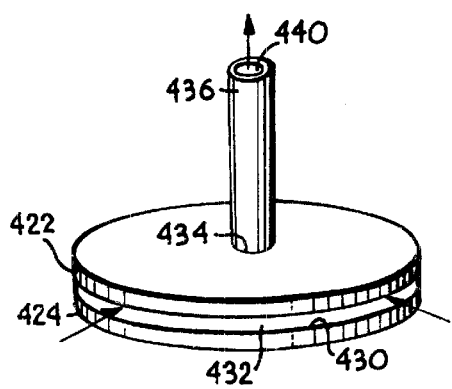
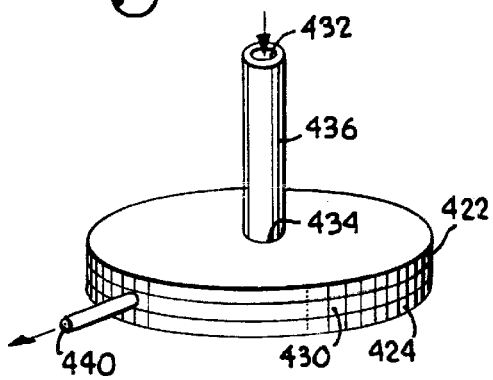
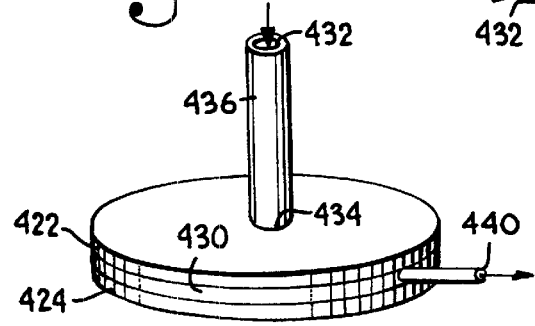
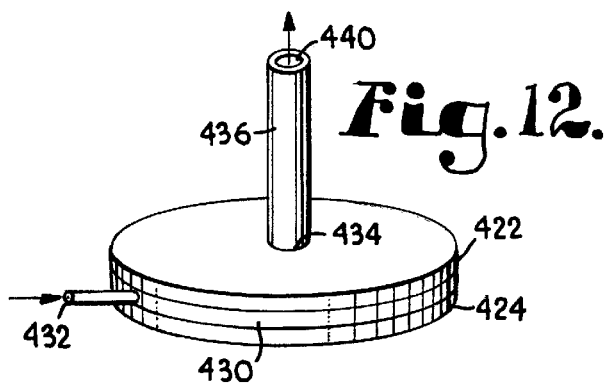
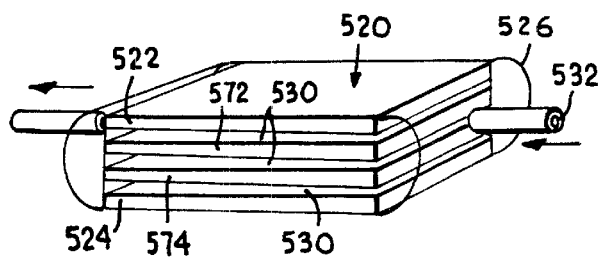
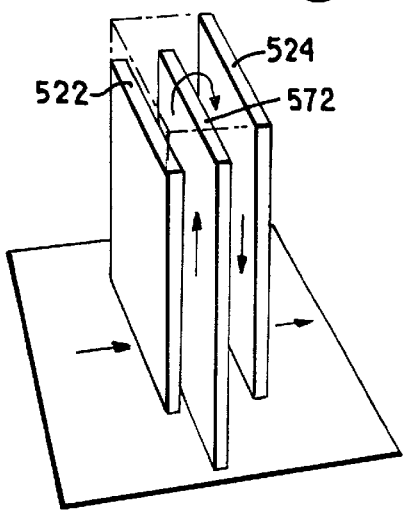

THERMOELECTRIC PARTICLE PRECIPITATOR AND METHOD USING SAME FOR COLLECTING PARTICLES FROM FLUID STREAMS

CROSS-REFERENCE TO RELATED APPLICATIONS

BACKGROUND OF THE INVENTION

The present invention relates to an apparatus for collecting fine particles from fluid streams and, more particularly, to a thermal precipitator having closely spaced apart, opposing hot and cold surfaces which cause such particles in a fluid stream in the spacing between the surfaces to undergo thermophoretic movement and precipitate on the cold surface of the thermal precipitator. The invention also relates to a method of using the thermal precipitator to collect or remove fine particles from fluid streams.

Sampling fine particles, i.e. those having less than 10 micron aerodynamic equivalent diameter (AED), from a fluid stream such as ambient air can be accomplished through a variety of methods. Dry cyclones, wet cyclones, scrubbers, impactors, and filters are a few methods conventionally available, but may have shortcomings in certain applications because they can affect the physical characteristics of the particles during the collection process. These physical alterations include mixing, spalling, agglomerating, compressing, dissolving or embedding of the particles into the collection medium. While such particle modifications may be acceptable if the particles are to be analyzed in bulk, they may not allow observers to categorize and examine the particulate matter as it is present in the atmosphere or other fluid stream. In addition, when collecting live biological particulate material, the analysis may require that the material remain viable. Many of the particle collectors referenced above apply stress to the biological material such that some or all of it is no longer biologically active. Moreover, these collectors have difficulty collecting ultrafine particles, i.e. less than 1 micron AED, making them poorly suited for applications where collection of ultrafine particles is required. Other disadvantages experienced by at least some of these collectors include pressure build-up as particles deposit on the collection surface, loss of collection fluid over an extended sampling time, and particle charging effects.

Conventional thermal precipitators provide a promising approach for collecting fine particles from air streams. Thermal precipitators have been documented to collect over 99.9 percent of particles less than 5 microns in diameter. Unlike other types of collectors, a thermal precipitator works better as the particle size decreases. Efficient collection of particles as low as 0.01 microns has been shown. Thermal precipitation is generally efficient for collecting articles smaller than 10 microns in diameter.

A thermal precipitator typically consists of a cooled plate and a heated plate separated by a very small distance that permits air containing suspended particles to flow in the space between the plates. At least a portion of the suspended particles precipitates on the surface of the cooled plate as a result of thermophoresis, a phenomenon where the kinetic energy of the air molecules drives the suspended particles from hotter areas to colder areas. Because of the temperature gradient between the cooled and heated plates, the net transfer of energy from the air molecules to the suspended particles tends to propel the particles from the warm (high energy) level to the cooler level, resulting in precipitation of the particles on the cooled plate. The migration of the suspended particles resulting from the thermal motion of the fluid molecules is referred to as Brownian movement.

The thermal precipitator collection method is very gentle to the collected particles in comparison to other collection methods and is not limited by buildup of high pressure as particles are collected, by particle impact and loss of viability of the collected particles, by loss of collection fluid over an extended length sampling time, or by particle charging effects. Moreover, particles are segregated by size on the cool particle collection surface, as small particles are precipitated first and larger particles are precipitated later. Only moderate temperature differences are needed to construct an efficient thermal precipitator.

One notable disadvantage of known thermal precipitator designs is the tendency to be bulky and cumbersome to transport and use. Thermal precipitators typically use water to provide cooling of the cooled plate and electrical resistance heating to provide heating of the heated plate. While this construction may be acceptable for use at fixed locations where water and electrical service are present, it severely limits the suitability of conventional thermal precipitators for use in remote, mobile or personal monitoring applications where small size, ready transportability and/or self-contained heating and cooling capability are required.

Thermoelectric modules are used to provide alternately cooled and heated surfaces using the physical principle, called the "Peltier Effect," where a direct current applied to a junction of two dissimilar materials causes one junction of the circuit to become cold while the other junction becomes hot. Practical considerations require that the two junction materials be metallic semiconductors. A variety of solid state junction materials have been developed and these are commercially available as thermoelectric modules from several vendors.

Thermoelectric modules are conventionally used to provide cooling of a heat transfer fluid, which in turn is used to provide heat transfer in cooling systems such as small refrigerators, air conditioners, cold traps for vacuum systems, cooling controls for thermocouple reference junctions, cooling devices for scientific equipment such as infrared detectors, cold stages on microscopes or on microtomes used for sectioning cooled tissues, and cooling electronic equipment. Thermoelectric modules can also be operated in reverse to convert heat energy into electric energy and have been used in power generation systems for spacecraft.

Thermoelectric cooling modules are commercially available in a variety of sizes and ratings. Cooling capacities range from 1 to 100 watts per module. A single stage module can typically generate 30–80° F. temperature difference, depending on the heat load conditions. Custom cooling applications can require multiple modules or a variety of heat transfer surfaces. When multiple modules are used, the cooled surface of one module is placed in contact with the heated surface of the adjacent module.

The attractiveness of thermoelectric cooling devices is that they are rugged and reliable solid state devices with no moving parts. They are silent, have minimal maintenance requirements and have long lifetimes (around 200,000 hours). For small cooling loads, thermoelectric devices can be much lighter and more compact than conventional vapor compression chillers. The device can be made small and very rugged for portable applications.

Although the prior art includes various thermal precipitators as fine particle collectors and thermoelectric modules as heat transfer or power generating devices, there exists a need for a particle precipitation device capable of collecting fine and ultrafine particles that is miniaturized, portable and consumes less power than traditional precipitators. The present invention fills these and other needs, and overcomes the short-comings of the prior art.

BRIEF SUMMARY OF THE INVENTION

It is an object of the invention to provide a thermal particle precipitator utilizing one or more thermoelectric modules that can be powered by batteries and do not require connection to water and external electrical sources at the collection site, so that the thermal precipitator can be readily transported and used at remote locations.

It is also an object of this invention to provide a thermoelectric particle precipitator using thermoelectric modules which can be of a small or miniaturized size so that the precipitator can be used as a nonobtrusive personal sampler.

It is another object of this invention to provide a thermoelectric particle precipitator as described which is of a small or miniaturized size and yet is of durable and rugged construction so that it can provide reliable operation even under extreme handling or environmental conditions.

It is a further object of this invention to provide a thermoelectric particle precipitator with a collection surface that integrates detection technology directly onto the collection surface so that in situ analysis can be performed on the collected particles.

It is a yet further object of this invention to provide a thermoelectric particle precipitator using thermoelectric modules that can be easily integrated into other equipment and used to produce clean air streams devoid of particles.

To accomplish these and other related objects, in one aspect, the invention is directed to a thermoelectric particle precipitator that removes and collects particles from a fluid stream using one or more thermoelectric modules. The thermoelectric module has first and second surfaces and is operable when the module is energized by direct current to cause cooling of the first surface and heating of the second surface. When a thermal mass is placed in a facing relationship to either the first or second surface of the thermoelectric module by a preselected and/or adjustable distance of separation, a temperature differential is formed between the thermal mass and the facing surface of the thermoelectric module. When the thermal mass is a heat source, it faces the cooled first surface of the thermoelectric module. Conversely, when the thermal mass is a heat sink, it faces the heated second surface of the module. A fluid flow passage is formed in the space between the thermal mass and the facing of the first or second surface of the thermoelectric module. An inlet is provided through which a fluid stream containing suspended particles is introduced into the fluid flow passage and an outlet allows the fluid stream to be removed from the fluid flow passage. The preselected distance of separation between the thermal mass and the facing surface of the thermoelectric module is effective when the temperature differential is formed to permit the particles in the fluid stream to undergo thermophoretic movement and collect on the cooler of the facing surfaces of the thermal mass and the thermoelectric module and thereby be removed from suspension in the fluid stream.

The thermal mass can be another thermoelectric module or, alternatively, it can be any other suitable source of heating or cooling, including ambient air. Movement of the fluid stream through the fluid flow passage can be induced by various means, including rotative movement of the one or more thermoelectric modules, fluid pumps and natural convection. The fluid stream can be ambient air or another gaseous medium, but may also include liquid mediums.

In another aspect, the invention is directed to a method of separating particles from suspension in a fluid stream using the described thermoelectric particle precipitator and then, optionally, analyzing the collected particles to determine their composition.

BRIEF DESCRIPTION OF THE DRAWINGS

In the accompanying drawings which form part of the specification and are to be read in conjunction therewith and in which like numerals are used to indicate like parts in the various views:

FIG. 1 is a top perspective view of a thermoelectric particle precipitator of the present invention with portions of the casing broken away to illustrate internal details of construction;

FIG. 2 is a front elevation view, taken in vertical section, of the thermoelectric particle precipitator shown in FIG. 1;

FIG. 3 is an enlarged, fragmentary elevation view, taken in vertical section, of a portion of the thermoelectric particle precipitator shown in FIG. 1;

FIG. 10 is a side perspective view of a fifth embodiment of a thermoelectric particle precipitator of the present invention;

FIG. 11 is a side perspective view of a variation of the thermoelectric particle shown in FIG. 10;

FIG. 12 is a side perspective view of another variation of the thermoelectric particle precipitator shown in FIG. 10;

FIG. 13 is a side perspective view of yet another variation of the thermoelectric particle precipitator shown in FIG. 12;

FIG. 14 is a side perspective open view of a sixth embodiment of a thermoelectric particle precipitator of the present invention;

FIG. 15 is a side perspective open view of a seventh embodiment of a thermoelectric particle precipitator of the present invention;

DETAILED DESCRIPTION OF THE INVENTION

Figure 4:
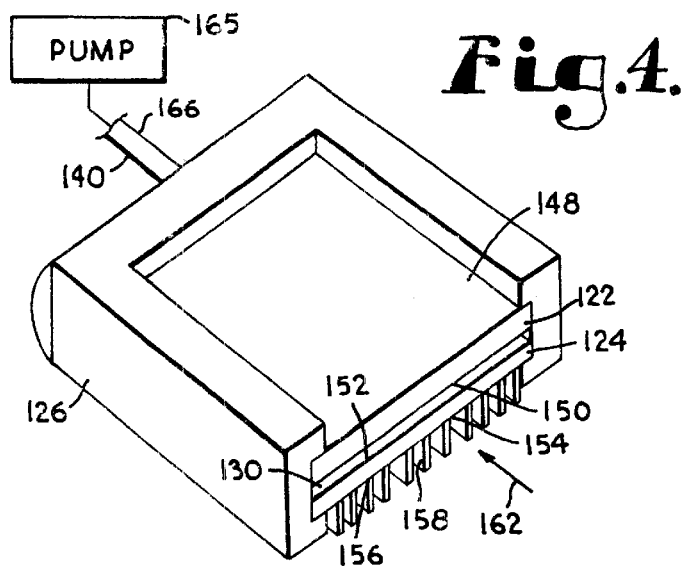
FIG. 4 is a top perspective view of a second embodiment of a thermoelectric particle precipitator of the present invention.
Figure 6:
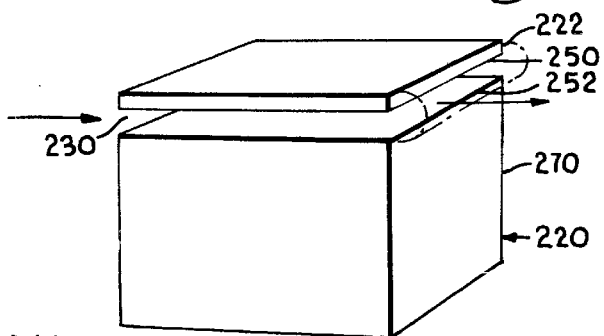
FIG. 6 is a side perspective view of a third embodiment of a thermoelectric particle precipitator of the present invention.

Turning now to the drawings in greater detail, and initially to FIGS. 1–3, a thermoelectric particle precipitator of the present invention is designated generally by reference numeral 20. The thermoelectric particle precipitator 20 is designed to remove particles from suspension in a fluid stream and collect them on a surface followed, optionally, by observation or further analysis or processing. In one embodiment, the thermoelectric particle precipitator 20 has a pair of closely spaced apart thermoelectric modules 22 and 24 positioned within a suitable housing 26. The thermoelectric modules 22 and 24 are disk-shaped and are maintained in a parallel stacked configuration with a preselected distance of separation between the facing surfaces of the modules. The modules are joined together by spacer bolts 28 that extend through the upper module 22 and are secured to the lower module 24. Suitable sleeves (not shown) carried on the bolts 28 may be used to maintain the desired distance of separation between the modules 22 and 24.

A fluid flow passage 30 is formed in the close s acing between the thermoelectric modules 22 and 24 and is defined by the facing surfaces of the modules. An inlet 32 to the fluid flow passage 30 is formed by a center opening 34 extending verticall through the upper module 22 and a cylindrical throat 36 that is fixed to the upper module 22 surrounding the center opening 34. The inlet throat 36 is of a preselected length and extends upright through a complementally shaped throat portion 38 of housing 26 to permit fluid from the surrounding environment to pass through the housing 26 and enter the fluid flow passage 30. The throats 36 and 38 also function as a bushing to facilitate rotation of the thermoelectric modules 22 and 24 in a manner to be subsequently described. A circular outlet 40 through which fluid exits the passage 30 is formed along and between the outer perimeters of the circular modules 24 and 26. A plurality of circumferentially spaced apart, slit-like openings 42 are formed in the housing 26 adjacent the outlet 40 to permit the fluid to be exhausted through the housing after passing through the fluid flow passage 30.

The thermoelectric modules 22 and 24 are solid state devices that convert electrical energy into a temperature gradient by virtue of a phenomenon known as the "Peltier Effect." The Peltier Effect occurs when a direct current is applied in one direction through a junction of two dissimilar materials, then one junction of the circuit becomes cold while the other becomes hot. Thermoelectric modules are commercially available and the details of construction are available from a variety of sources. For example, typical thermoelectric modules comprise two ceramic substrates that serve as a foundation and electrical insulation for P-type and N-type bismuth telluride dice that are connected electrically in series and thermally in parallel between the ceramic substrates. Copper pads or other electrically conductive materials maintain electrical connections within the module. Direct electric current is provided to operate the modules from a power source such as batteries, AC/DC converters and battery chargers. In the illustrated embodiment, DC power is supplied by batteries 44 which are housed within compartments 45 formed at opposite ends of the housing 26 and are in electrical contact with the thermoelectric modules 22 and 24. Electric leads 46 connect the batteries 44 and modules 22 and 24 with a controller 47 that regulates operation of the precipitator 20.

The upper thermoelectric module 22 has a first or upper surface 48 and an opposite second or lower surface 50. Similarly, the lower thermoelectric module 22 has a first or upper surface 52 that faces the lower surface 50 of upper module 22 and an opposite second or lower surface 54. The modules 22 and 24 are wired in one embodiment so that, when supplied with direct current, the upper surfaces 48 and 52 of the modules are cooled and the lower surfaces 50 and 54 of the modules are heated. In this manner, the facing surfaces 52 and 54 which form the fluid flow passage 30 are of different temperatures and form a vertical temperature gradient across the passage 30. As will be subsequently described in greater detail, this temperature gradient causes particles suspended in a fluid stream flowing through the passage 30 to undergo thermophoretic movement and be deposited on the cooled upper surface 52 of the lower module 24. When the electric current to the modules 22 and 24 is reversed, it will be appreciated that the heating and cooling of the modules surfaces will also be reversed and thermophoretic precipitation will occur on the cooled lower surface 50 of upper module 22. Normally, when the module 22 is subject to the effects of gravity, direct current is supplied in a manner to cause cooling of the upper surface 52 of the lower module 24 so that particle precipitation occurs on the cooled upper surface 52. In applications where gravity is of reduced or no effect, such as in space, the direction of current flow is of less importance. The degree of heating or cooling of the surfaces can be increased by stacking one or more additional thermoelectric modules in contact with the modules 22 and 24 in a known fashion.

A heat sink 56 is attached to the lower surface 54 of lower module 24 to remove heat from the lower surface 54 and thus ensure the desired cooling of upper surface 52. The heat sink 56 comprises any suitable thermally conductive material such as aluminum or copper and includes a plurality of spaced-apart fins or blades 58 for increased surface area.

In one embodiment, fluid flow through the fluid flow passage 30 is induced by rotation of the thermoelectric modules 22 and 24 within the housing 26. This rotation can be accomplished in any suitable manner, such as by using a D.C. motor 60 centrally mounted beneath the lower module 24 and operated by batteries 44. A vertically extending shaft (not shown) from the motor 60 is connected to the lower module 24 and operates to rotate the modules about a center vertical axis. Rotation of the modules in this manner not only serves to induce fluid flow in the direction of arrows 62 in FIG. 3, but also facilitates transfer of heat from heat sink 56.

The size of the thermoelectric particle precipitator 20 can be varied as needed for any desired size application. Miniaturization of the precipitator 20 to a size of 3 cm or less can be readily accomplished with conventional manufacturing techniques and makes the precipitator readily transportable. The portable, self-contained nature of the precipitator makes it highly desirable for personal and mobile sampling applications where conventional thermal precipitators would be difficult to use because of their bulk and the need for connection to water and electrical services.

In operation, the thermoelectric particle precipitator 20 is placed in an environment where sampling or removal of particles from a fluid stream is desired. In many applications, the fluid stream will be ambient air or another gaseous medium. It is also contemplated, however, that the precipitator 20 can be used to collect particles suspended in a liquid stream. Once located in the intended environment, direct current is supplied to the electric circuit by insertion of the batteries into the compartments 46 and, optionally, moving a circuit switch (not shown) to an “on” position. The direct current supplied to the thermoelectric modules 22 and 24 causes cooling of upper surfaces 48 and 52 and heating of lower surfaces 50 and 54, thereby forming a vertical temperature gradient across the fluid flow passage 30. The direct current also operates the motor 60 to induce horizontal rotation of the coupled modules 22 and 24 about the center vertical axis. This rotation of the modules induces the fluid stream to flow in the direction of arrows 62 through the inlet throat 36 and center opening 34 of module 22 into the fluid flow passage 30. The fluid stream then flows in a spiral fashion from the center of the passage to the perimeter outlet 40 where it is discharged from the housing through openings 42.

As the fluid stream flows along the fluid flow passage 60, particles which are suspended in the fluid stream undergo thermophoresis as a result of the temperature gradient formed by the heated surface 50 and the facing cooled surface 52 of thermoelectric modules 22 and 24, respectively. Thermophoresis causes the suspended particles to move in the direction of the cooled surface 52 where particles within a preselected range of sizes are precipitated or deposited on the cooled surface. The size range of deposited particles can be controlled by a number of variables, such as the magnitude of the temperature gradient, the spacing between the module surfaces 50 and 52, and the flow rate of the fluid stream. In general, the distance of separation between the facing surfaces 50 and 52 of the modules will be within the general range of 0.01 cm to 2.0 cm, and more preferably, within the range of 0.03 cm to 0.2 cm. It is to be understood that these are only general guidelines and the distance of separation may deviate from these parameters depending upon fluid flow rate, thermal gradient, and desired particle size to be collected.

Once the preselected sampling time has been completed, the particles which have collected on the cooled surface 52 can be observed and analyzed in the desired manner, such as to determine the presence and quantity of particular compounds. For example, when used as a personal monitor to determine exposure to a particular pollutant, the cooled surface 52 may be analyzed to determine the amount of pollutant present on the collection surface. For example, the mass of the pollutant can be measured in situ when a quartz crystal microbalance is attached to the cooled collection surface 52. Analysis of the cooled surface 52 can take place in a variety of different ways, such as by microscopy, visual observation or other analysis of the surface 52 or by removal of the particles from the surface 52 by scraping, swabbing or rinsing with a carrier fluid for subsequent analysis. To facilitate removal of the particles from surface 52, it may be desirable in certain instances to reverse the direction of current flow to the thermoelectric modules 22 and 24 to cause heating rather than cooling of the upper surface 52 of the lower module 24 and then flowing an inert carrier fluid through the passage 30 to pick up particles or disrobed vapors which have been released from the surface 52.

The precipitated particles can be collected directly on the cooled surface 52 of the lower thermoelectric module 24 or on a collection substrate 64 which is coated on or applied to the cooled surface 52 to aid in the removal and/or analysis of collected particles. The upper surface of the collection substrate 64 can be either porous or smooth, whichever provides the best collection or analytical efficiency for the intended application. The collection substrate 64 can be made of metal, silicon compound or organic materials, including a cellulose or a water soluble organic material such as xylitol, ribose, sucrose and the like. A suitable coating can be used to preserve the viability and/or stability of the precipitated particles, particularly in the case of collected biomaterials.

If the collection substrate 64 is a thin cellulose film, the film is removed from the cooled surface 52 of the lower thermoelectric module 24 after sampling, and enzymatically digested in solution with a cellulase. The enzymatic digestion of cellulose provides for nearly 100% elution of collected particulate into solution for analysis. The type of cellulose used is such that its enzymatic digestion does not decrease the viability of collected bioaerosol particles.

The collection substrate 64 may alternatively be a thin film of a water soluble organic material. After sampling, the thin water soluble organic film is removed and dissolved in a water-based buffer solution to allow for 100% elution of collected particulate. The type of water soluble organic material used to construct the film is such that it does not have negative effect on the viability of bioaerosol particles during the collection or elution steps.

In certain applications, it may be desirable to require disassembly of the precipitator using special tools in order to reduce the opportunity for tampering with the particles which have precipitated on the cooled surface 52. In other applications, it may be desirable to provide rapid analysis and detection of the precipitated particles without requiring disassembly of the precipitator 20. Because the cooled upper surface 52 of the lower thermoelectric module 24 acting as the collection surface of the precipitator 20 is a solid surface, it is possible to integrate detection technology directly into the upper surface 52 using biosensors (not shown) which combine the assay chemistry and detector functions. These sensors may include one or more electrochemical, biological, optical, acoustic, thermal and physical (based on electrical impedance) devices, including lab-on-a-chip microchips where analysis is carried out wholly or partially within the confines of the microchip. The lab-on-a-chip can be integrated with the thermoelectric module and may incorporate sample collection, sample preparation (including sample recovery and physical, chemical, or biological separation), and analysis on a single, integrated substrate. The sample can be transported to different areas on the chip (reaction "wells", microscopic vessels, etc.) by micro-fluidic techniques and processed as necessary. Any of these types of sensors can be integrated into the cooled upper surface 52 of the lower thermoelectric module 24 to provide near simultaneous collection and detection of preselected particles such as bioaerosols.

The fluid stream is preferably in laminar flow to allow for efficient precipitation of the suspended particles, but turbulent flow may also be utilized. Because the thermoelectric modules 22 and 24 are fixed together by bolts 28, they rotate in the same direction and at the same velocity, thereby creating a laminar flow of the fluid stream in the fluid flow passage 30 in the space between the two modules 22 and 24. Notably, the rotating modules 22 and 24 induce fluid stream flow without pulses, vibration, sudden pressure change, rapid directional change, or impact. The pumped fluid is accelerated smoothly and in a radially increasing dimension. The pumping effect is achieved by the friction, adhesion and shear generated between the fluid stream and the facing surfaces 50 and 52 of the modules.

It will be appreciated that the thermoelectric particle precipitator can also be used to cleanse or purify a fluid stream by removing particles from suspension in the fluid streams. This is contemplated by and is within the scope of the invention.

Figure 5:
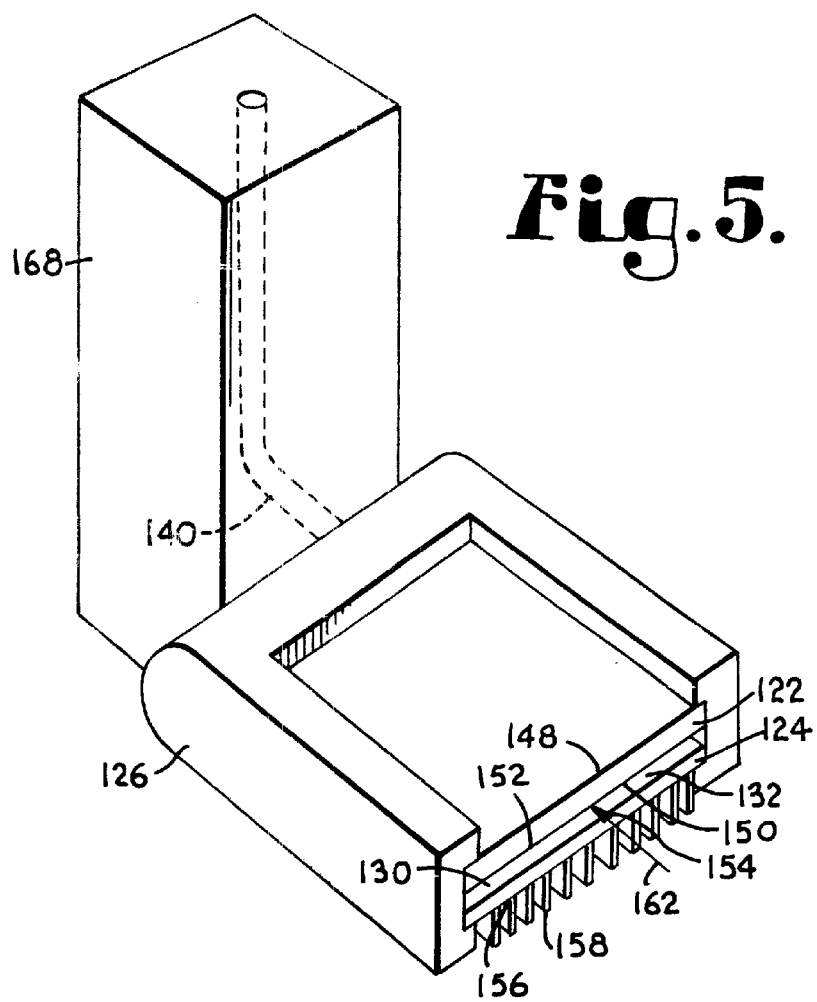
FIG. 5 is a top perspective view of a variation of the thermoelectric particle precipitator shown in FIG. 4.

Several variations of the thermoelectric particle precipitator of the present invention are shown in FIGS. 4–15, illustrating different ways that the thermoelectric modules can be utilized to achieve the temperature gradient needed for particulate collection. Referring first to FIGS. 4 and 5, an upper thermoelectric module 122 and a lower thermoelectric module 124 are oriented parallel to each other in closely spaced relationship and are slidably mounted in a housing 126 of plexiglass or other any insulating material. A fluid flow passage 130 is formed in the space between the modules 122 and 124, with an inlet 132 to the passage being formed along and between a forward edge of the square-shaped modules 122 and 124 and an outlet 140 being formed along an opposite edge of the modules.

The thermoelectric modules 122 and 124 can be operated in the manner previously described. When energized by a power source, upper surfaces 148 and 152 of the thermoelectric modules 122 and 124, respectively, are cooled while lower surfaces 150 and 154 are heated. This temperature differential creates a temperature gradient in the fluid flow passage 130 located between the modules 122 and 124. As air is pulled through the inlet 132, particles suspended in the air stream undergo thermophoretic movement that cause them to be deposited on the cooled upper surface 152 of the lower thermoelectric module 124. A heat sink 156, which includes fins 158 and a fan (not shown), is used to draw heat away from the lower surface 154 of the lower thermoelectric module 124 to facilitate cooling of the upper surface 150 of the module 124.

In the embodiment shown in FIG. 4, movement of the fluid stream in the direction of arrow 162 is induced by a fluid pump, represented schematically by the numeral 165, connected to an outlet plenum 166 to draw the fluid stream through the inlet 132 and into the fluid flow passage 130. It will, of course, be appreciated that the flow of electric current to the thermoelectric modules could be reversed to cause a reversal of the heated and cooled surfaces so that particles will precipitate on the cooled lower surface 150 of the upper module 122. The flow of the fluid stream can also be reversed by using the pump 165 to push rather than pull air through the fluid flow passage 130.

In the embodiment shown in FIG. 5, the need for a fluid pump is eliminated by utilizing a heated outlet 168 to draw the fluid stream through the fluid flow passage 130 using natural convection.

Although the thermoelectric particle precipitators described above utilize two spaced apart thermoelectric modules to obtain the desired temperature gradient required for thermophoretic movement of the particles in the fluid stream, the present invention also contemplates that the temperature gradient can be formed using a thermoelectric module at one end of the gradient and a thermal mass other than a thermoelectric module at the other end of the gradient. This is illustrated somewhat schematically in FIGS. 6 and 7 where a thermal mass which may be a solid or fluid is used in place of a second thermoelectric module. In the embodiment illustrated in FIG. 6, a thermoelectric particle precipitator 220 is created utilizing an upper thermoelectric module 222 and a spaced apart thermal mass 270 which acts as a heat sink. The thermal mass can be any suitable solid and provides an upper surface 252 that is cooled in comparison to the heated lower surface 250 of the upper module 222 which is obtained when the module 222 is energized. The temperature gradient formed between the surfaces 252 and 250 causes thermophoretic movement of particles in the fluid stream flowing through the fluid flow passage 230, resulting in precipitation of particles on the cooled upper surface 252 of the thermal mass. If the electrical current to the upper module 222 is reversed, the lower surface 250 becomes cooled and the thermal mass can be formed from any suitable solid or fluid that will provide the necessary temperature gradient to cause precipitation of particles on the cooled lower surface 250 of module 222.

Figure 7:
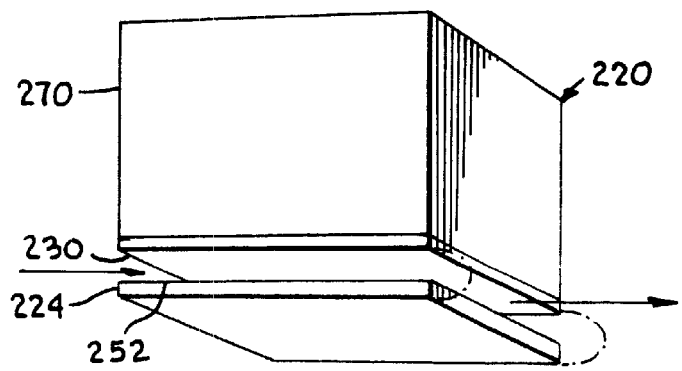
FIG. 7 is a side perspective view of a variation of the thermoelectric particle precipitator shown in FIG. 6.

In the embodiment illustrated in FIG. 7, a lower thermoelectric module 224 is used and the thermal mass 270 is used in place of the upper thermoelectric module 222. In a manner similar to that described with respect to the FIG. 6 embodiment, the thermal mass 270 can be a solid or fluid that provides the necessary heat sink or heat source so that a temperature gradient is obtained between the thermal mass and the heated or, alternately, cooled upper surface 252 of the lower module 224. Examples of suitable heat sinks and heat sources can be devices such as evaporating water coolers, electric resistance heaters, solar heated masses, and ambient air.

Figure 8:
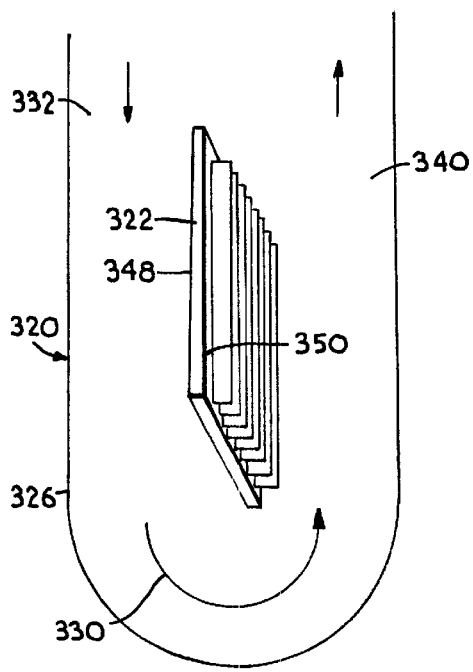
FIG. 8 is a side perspective view of a fourth embodiment of a thermoelectric particle precipitator of the present invention.
Figure 9:
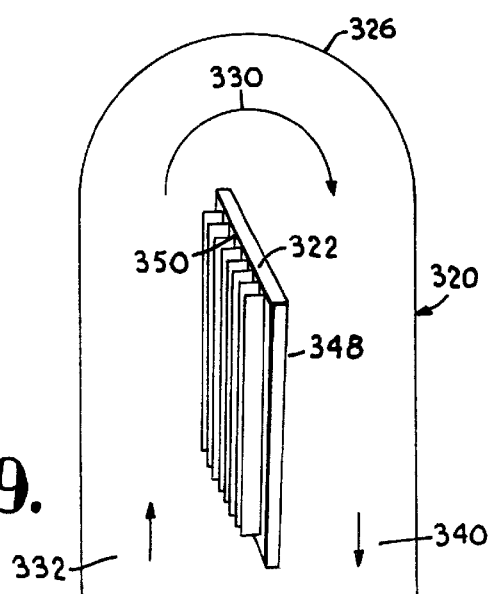
FIG. 9 is a side perspective view of a variation of the thermoelectric particle precipitator shown in FIG. 8.

The present invention also contemplates that the temperature differential across the thermoelectric module itself can be utilized to induce flow of the fluid stream through the fluid flow passage. Referring to FIGS. 8 and 9, a thermoelectric particle precipitator 320 is formed by a single thermoelectric module 322 placed into a ventilated housing 326 that is open at one end so that the fluid stream can flow across one surface of the module in one direction and then flow across the opposite surface of the module in the reverse direction. In the precipitator 320 shown in FIG. 8, the ventilated housing 326 has an opening at the top which forms both an inlet 332 and outlet 340 for a fluid flow passage 330. At the inlet 332, fluid sinks downwardly along the cooled surface 348 of the module and suspended particles in the fluid stream are deposited on the cooled surface 348. The fluid stream is then heated by the opposite heated surface 350 of the module and rises for discharge through the outlet 340. The cooled and heated surfaces 348 and 350 of the module thus establish a natural circulation of the fluid stream through the fluid flow passage 330.

In the embodiment shown in FIG. 9, the ventilated housing 326 has an opening at the bottom and the fluid stream first flows upwardly along the heated surface 350 and then downwardly along the cooled surface 348 of module 322. As previously described, the particles are then precipitated on the cooled surface 348.

In the thermoelectric particle precipitators illustrated in FIGS. 10–13, disk-shaped thermoelectric modules 422 and 424 similar to those described with respect to the FIG. 1 embodiment are used. The modules 422 and 424 are placed parallel to one another with the upper module 422 having a circular center opening 434 and cylindrical throat 436 which form either the inlet 432 or outlet 440 for the fluid flow passage 430. In FIG. 10, fluid is drawn downwardly through the throat 436 and opening 434 and flows radially outward to an outlet 440 formed along and between the peripheral edge of the modules 422 and 424. In FIG. 11, the direction of fluid flow is reversed as it is pulled through a peripheral inlet 432 and radially inwardly through the flow passage 430 and then up through the center opening 434 and throat 436. A tangentially directed inlet 432 is illustrated in FIG. 12 and creates a cyclonic rather than radial fluid flow pattern. FIG. 13 shows the cyclonic air flow pattern reversed from that illustrated in FIG. 12.

It will be appreciated that higher sampling rates and available surface area for precipitation of particles can be achieved by using multiple thermoelectric modules to define more than one fluid flow passage. In the thermoelectric particle precipitator embodiments shown in FIGS. 14 and 15 multiple thermoelectric modules are used to form both serial and parallel fluid flow passages arranged horizontally as well as vertically. In FIG. 14, upper and lower thermoelectric modules 522 and 524 and two intermediate modules 572 and 574 extending horizontally in vertically spaced apart relationship. The modules are mounted within housing 526 of plexiglass or other insulating material and an inlet 532 at one end of the housing 526 feeds fluid into the plurality of parallel fluid flow passages 530. An outlet 540 at the opposite end of the housing 526 permits removal of the fluid stream from the precipitator 520 following precipitation of the suspended particles on the cooled upper surfaces of the modules or, alternatively, on the cooled lower surfaces of the modules. In FIG. 15 the modules 522, 572 and 524 are arranged so that the fluid stream flows in one direction and then reverses course to flow in the opposite direction as a result of natural ventilation, with particle precipitation occurring on two cooled surfaces. It will be appreciated that additional modules could be utilized to create a serpentine fluid flow pattern with particle precipitation occurring on multiple cooled surfaces.

Figure 16:
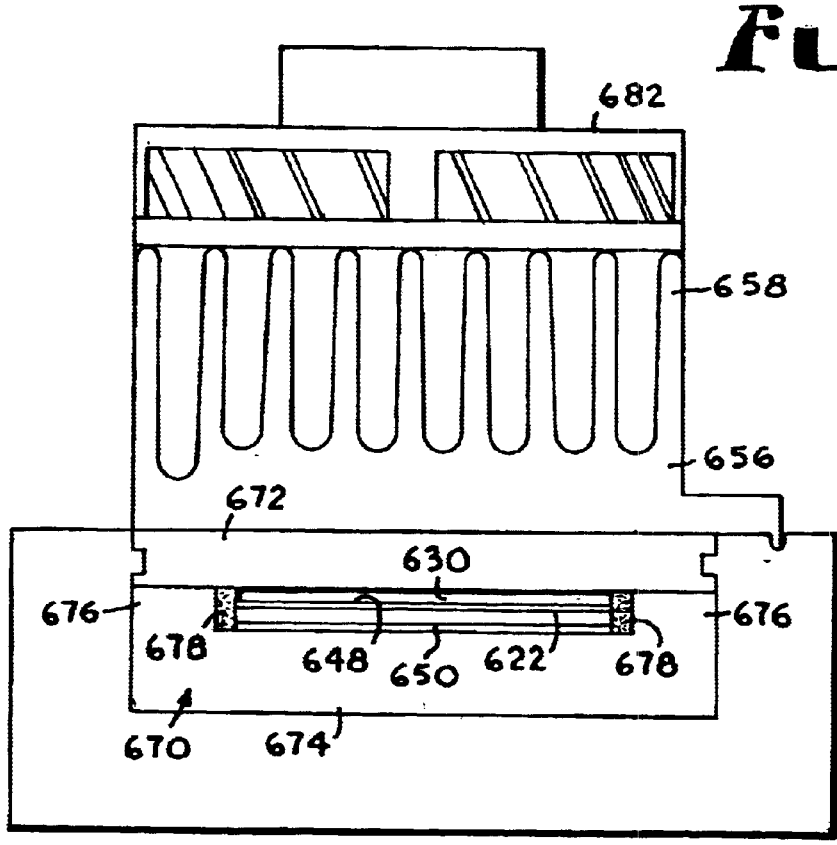
FIG. 16 is a side elevation view of an eighth embodiment of a thermoelectric particle precipitator of the present invention.

In another variation of the present invention, the heat generated at the heated surface of the thermoelectric modules described herein can be captured and transferred to the thermal mass facing the cooled collection surface of the module. In this manner, the temperature gradient across the fluid flow passage is created or enhanced by the transfer of heat generated by the module itself. This concept is illustrated in FIG. 16 in which a thermal mass 670 formed from a thermally conductive material, such as one or more metals, surrounds a thermoelectric module 622. The thermal mass 670 includes an upper plate 672 that is spaced above a cooled upper surface 648 of the thermoelectric module 622 to form a fluid flow passage 630 in the open space between the upper plate 672 and module upper surface 648. The thermal mass 670 also includes a lower plate 674 that is in thermal contact with a heated lower surface 650 of thermoelectric module 622. The thermal mass 670 also includes sides 676 that join the edges of the upper and lower plates 672 and 674 and allow heat transfer between the upper and lower plates. Thermal insulators 678 are placed between the thermal mass 670 and the sides of the thermoelectric module 622 to prevent undesired heat transfer between the thermal mass 670 and the cooled upper surface 648 of the module 622. If desired, the thermal mass 670 may itself be thermally insulated from the surrounding ambient fluid by placement of an optional layer 680 of insulative material against the exposed bottom and sides of the thermal mass 670.

The configuration of the components of the thermal mass 670 is not limited to that illustrated in FIG. 16. For example, upper plate 672, sides 676 and lower plate 674 can be of a one piece construction. Alternatively, the thermal mass 670 can be formed by C-shaped elements which face each other.

In use, the lower plate 674 of the thermal mass 670 absorbs heat from the lower surface 650 of the thermoelectric module 622 and conveys it through sides 676 to the upper plate 672 where it creates a temperature gradient vertically across the fluid flow passage 630. In order to facilitate heat transfer between the module lower surface 650 and thermal mass lower plate 674, a coating of thermal grease or past can be applied to the contacting surfaces. In the manner previously described, particles suspended in the air stream flowing through the passage 630 undergo thermophoretic movement that causes them to be deposited on the cooled upper surface 648 of thermoelectric module 622.

In order to regulate the temperature of the upper plate 672 of the thermal mass 670, a heat sink 656 having a plurality of heat transfer fins or blades 658 is positioned on top of the upper plate 672. A fan 682 may be positioned to draw or push air or another heat transfer fluid across the heat sink 656 and can be selectively activated in response to temperature sensors (not shown) located to detect and control the temperature gradient across the fluid flow passage 630.

Figure 17:
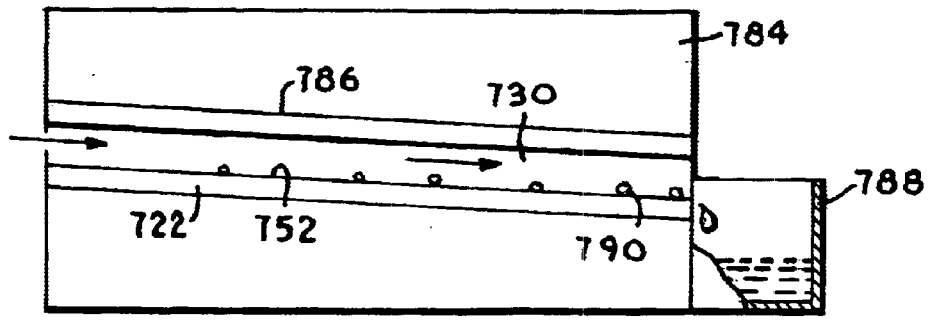
FIG. 17 is a side perspective view of a ninth embodiment of a thermoelectric particle precipitator of the present invention.

The present invention also contemplates using the heat generated by the battery and electronic components associated with the thermoelectric particle precipitator to create or contribute to the temperature gradient across the fluid flow passage. This is schematically illustrated in FIG. 17, wherein a battery 784 is spaced above a cooled upper surface 752 of a thermoelectric module 722. Heat generated by the battery 784 forms a temperature gradient across the fluid flow passage 730 formed in the open space between the battery 784 and the module upper surface 752. If desired, electronic control elements 786 may be positioned above or below the battery 784 and the heat from the electronic control elements 786 contributes to the temperature gradient.

It will also be appreciated that condensate droplets may be collected with the particles deposited on the cooled upper surface of the thermoelectric module. To facilitate analysis of these droplets with entrained particles, the cooled upper surface of the module can be tilted downwardly in the direction of a collector so that the droplets will move under the influence of gravity into the collector. This concept is illustrated in FIG. 17, wherein the cooled upper surface 752 of the module 722 slopes downwardly in the direction of a collector 788. The slope of the upper surface 752 can be in the longitudinal direction of air flow in passage 730 to direct droplets 790 into the collector 788 positioned at the longitudinal end of the upper surface 752. Alternatively, the slope can be in a direction transverse to the direction of air flow, with the collector 788 being positioned along the side rather than the end of the upper surface 752. Mechanical forces such as a vibratory force from a piezoelectric element may optionally be used to assist movement of the droplets 790 in the desired direction. The collected droplets 790 and particles can then be analyzed in any of the manners previously described.

Although the upper surface of the thermoelectric module and the facing surface of thermal mass are parallel in the illustrated embodiments, it is to be understood that they can extend in a non-parallel relationship and can be fixed or variable in their orientation. In addition, a thermal mass can also be placed in thermal communication with the cooled surface of the thermoelectric module in order to provide greater thermal inertia and facilitate temperature uniformity and maintenance along the fluid flow passage.

From the foregoing, it will be seen that this invention is one well adapted to attain all the ends and objects hereinabove set forth together with other advantages that are inherent to the structure.

It will be understood that certain features and subcombinations are of utility and may be employed without reference to other features and subcombinations. This is contemplated by and is within the scope of the claims.

What is claimed is:

1. A thermal particle precipitator for removing and collecting particles from a fluid stream, said precipitator comprising:

a thermoelectric module having first and second surfaces and operable upon application of a direct current to provide cooling of said first surface and heating of said second surface;

a thermal mass comprising a heat sink having a surface spaced apart in a facing relationship to said second surface of said thermoelectric module by a preselected distance of separation, said surface of the heat sink having a lower temperature than the facing second surface of the thermoelectric module to form a temperature differential between said surface of the heat sink and said second surface of said thermoelectric module when said thermoelectric module is operated to provide cooling of said first surface and heating of said second surface; and a fluid flow passage formed in the spacing between said surface of the heat sink and the second surface of said thermoelectric module and having an inlet through which a fluid stream containing suspended particles is introduced into said fluid flow passage for travel along and between said surface of the heat sink and the second surface of said thermoelectric module and an outlet through which said fluid stream is removed from said fluid flow passage, wherein said preselected distance of separation between said surface of the heat sink and the second surface of said thermoelectric module is effective, when said temperature differential is formed, to permit the particles in the fluid stream to undergo thermophoretic movement and collect on said surface of the heat sink and be removed from suspension in the fluid stream.

2. The thermal particle precipitator of claim 1, wherein said inlet is located at one end of said thermoelectric module and said thermal mass and, wherein said outlet is located at an opposite end of said thermoelectric module and said thermal mass.

3. The thermal particle precipitator of claim 1, wherein said thermoelectric module is disk-shaped and a center opening is provided through said module to provide said inlet or said outlet.

4. The thermal particle precipitator of claim 1, including a pump in fluid flow communication with said fluid flow passage for inducing flow of said fluid stream.

5. The thermal particle precipitator of claim 1, wherein said thermoelectric module is mounted for rotative movement.

6. The thermal particle precipitator of claim 1, wherein said surface of the heat sink includes a removable or embedded particle collection substrate.

7. The thermal particle precipitator of claim 6, wherein said collection substrate includes a sensor.

8. The thermal particle precipitator of claim 7, wherein said sensor is electrochemical.

9. The thermal particle precipitator of claim 7, wherein said sensor is optical.

10. The thermal particle precipitator of claim 7, wherein said sensor is acoustic.

11. The thermal particle precipitator of claim 7, wherein said sensor is thermal.

12. The thermal particle precipitator of claim 4, wherein said surface of the thermal mass is spaced from and faces the first surface of the thermoelectric module and wherein said thermal mass is in thermal communication with said second surface to transfer heat from said second surface to said portion of the thermal mass facing the first surface of the thermoelectric module.

13. The thermal particle precipitator of claim 12, wherein said thermal mass comprises a bottom plate in contact with said second surface of the thermoelectric module and a top plate which forms said first portion of the thermal mass which is spaced from and faces the first surface of the thermoelectric module, said thermal mass further including one or more sides connecting said bottom plate to said top plate.

14. The thermal particle precipitator of claim 13, include a layer of insulation contacting an outer surface of said thermal mass.

15. The thermal particle precipitator of claim 4, including a battery operatively coupled with said thermoelectric module to provide a direct current thereto, wherein said battery is positioned in thermal communication with said thermal mass to transfer heat thereto.

16. The thermal particle precipitator of claim 15, wherein said thermal mass comprises an outer portion of said battery.

17. The thermal particle precipitator of claim 7, wherein said sensor is biological.

18. A method for removing and collecting particles from a fluid stream comprising: creating a temperature gradient between a thermoelectric module and a thermal mass; flowing a fluid stream containing suspended particles through said temperature gradient to cause said suspended particles to undergo thermophoretic movement in the direction of a cooler end of the temperature gradient; collecting at least a portion of said suspended particles on a surface of said thermoelectric module or said thermal mass as a result of said thermophoretic movement; and analyzing said particles collected on said surface.

19. The method of claim 18, including using another thermoelectric module as said thermal mass.

20. The method of claim 19, including creating said temperature gradient between a cooled surface of one of the thermoelectric modules and a heated surface of the other of the thermoelectric modules and wherein said cooled surface comprises said surface on which the suspended particles are collected.

21. The method of claim 18, including analyzing said particles collected on said surface.

22. The method of claim 18, including the step of supplying a collection substrate as said surface of the thermoelectric module or said thermal mass on which said suspended particles are collected.

23. The method of claim 22, wherein the step of supplying a collection substrate comprises supplying a collection substrate selected from the group consisting of a metal, a silicon compound or an organic material.

24. The method of claim 22, wherein the step of supplying a collection substrate comprise supplying a coating an organic material.

25. The method of claim 24, wherein the step of supplying a coating comprising an organic material comprises supplying a coating comprising cellulose, xylitol, ribose or sucrose.

26. The method of claim 24, wherein the step of supplying a coating of an organic material comprising supplying a coating comprising a cellulose material.

27. The method of claim 25, wherein said step of analyzing said particles collected on said surface includes the step of removing said coating with said collected particles and enzymatically digesting said removed coating in solution with cellulase.

28. The method of claim 22, wherein said step of supplying a collection substrate comprises supplying a coating comprising a water soluble organic material.

29. The method of claim 28, wherein said step of analyzing said particles collected on said surface includes the step of removing said coating with said collected particles and dissolving said removed coating in a water-based buffer solution.

30. The method of claim 22, including the step of providing a sensor on said surface for analyzing said particles collected on said surface.

31. The method of claim 30, wherein said step of providing a sensor comprises providing a sensor selected from the group consisting of electrochemical, optical, acoustic, thermal and biological sensors.

32. The method of claim 30, wherein said step of providing a sensor comprises providing a microchip comprising a biological sensor.

33. The method of claim 22, including the step of collecting condensation droplets on said surface with some of said suspended particles entrained within said condensation droplets.

34. The method of claim 33, including the step of moving said condensation droplets from said surface into a collector.

35. The method of claim 33, including the step of analyzing said condensation droplets.

36. A thermal particle precipitator for removing and collecting particles from a fluid stream, said precipitator comprising:

a thermoelectric module having first and second surfaces and operable upon application of a direct current to provide cooling of said first surface and heating of said second surface;

a thermal mass spaced apart in a facing relationship to said first or second surface of said thermoelectric module by a preselected distance of separation sufficient to form a temperature differential between said thermal mass and said first or second surface of said thermoelectric module when said thermoelectric module is operated to provide cooling of said first surface and heating of said second surface;

a fluid flow passage formed in the spacing between said thermal mass and the facing one of said first or second surfaces of said thermoelectric module and having an inlet through which a fluid stream containing suspended particles is introduced into said fluid flow passage for travel along and between said thermal mass and the facing one of said first or second surfaces of said thermoelectric module and an outlet through which said fluid stream is removed from said fluid flow passage, wherein said preselected distance of separation between said thermal mass and the facing of said first or second surfaces of said thermoelectric module is effective, when said temperature differential is formed, to permit the particles in the fluid stream to undergo thermophoretic movement and collect on said thermal mass or said first surface of said thermoelectric module and be removed from suspension in the fluid stream; and a heat sink attached in thermal communication with said second surface of said thermoelectric module to draw heat from said second surface of thermoelectric module.

37. The thermal particle precipitator of claim 36, including a sensor associated with said surface of the heat sink for analyzing said collected particles.

38. The thermal particle precipitator of claim 37, wherein said sensor is selected from the group consisting of electrochemical, optical, acoustic, thermal and biological sensors.

39. The thermal particle precipitator of claim 36, including a microchip comprising a biological sensor associated with said surface of the heat sink for analyzing said collected particles.

40. A thermal particle precipitator for removing and collecting particles from a fluid stream, said precipitator comprising:

a disk-shaped thermoelectric module having first and second surfaces and operable upon application of a direct current to provide cooling of said first surface and heating of said second surface;

a center opening through the first or second surface of the thermoelectric module;

a thermal mass spaced apart in a facing relationship to said first or second surface of said thermoelectric module by a preselected distance of separation sufficient to form a temperature differential between said thermal mass and said first or second surface of said thermoelectric module when said thermoelectric module is operated to provide cooling of said first surface and heating of said second surface; and a fluid flow passage formed in the spacing between said thermal mass and the facing one of said first or second surfaces of said thermoelectric module and having an inlet through which a fluid stream containing suspended particles is introduced into said fluid flow passage for travel along and between said thermal mass and the facing one of said first or second surfaces of said thermoelectric module and an outlet through which said fluid stream is removed from said fluid flow passage, wherein said preselected distance of separation between said thermal mass and the facing of said first or second surfaces of said thermoelectric module is effective, when said temperature differential is formed, to permit the particles in the fluid stream to undergo thermophoretic movement and collect on said thermal mass or said first surface of said thermoelectric module and be removed from suspension in the fluid stream.

41. The thermal particle precipitator of claim 40, including a sensor associated with said first surface of the thermoelectric module for analyzing said collected particles.

42. The thermal particle precipitator of claim 41, wherein said sensor is selected from the group consisting of electrochemical, optic, acoustic, thermal and biological sensors.

43. The thermal particle precipitator of claim 40, including a microchip comprising a biological sensor associated with said first surface of the thermoelectric module for analyzing said collected particles.

44. A thermal particle precipitator for removing and collecting particles from a fluid stream, said precipitator comprising:

a thermoelectric module having first and second surfaces and operable upon application of a direct current to provide cooling of said first surface and heating of said second surface;

a thermal mass spaced apart in a facing relationship to said first or second surface of said thermoelectric module by a preselected distance of separation sufficient to form a temperature differential between said thermal mass and said first or second surface of said thermoelectric module when said thermoelectric module is operated to provide cooling of said first surface and heating of said second surface;

a fluid flow passage formed in the spacing between said thermal mass and the facing one of said first or second surfaces of said thermoelectric module and having an inlet through which a fluid stream containing suspended particles is introduced into said fluid flow passage for travel along and between said thermal mass and the facing one of said first or second surfaces of said thermoelectric module and an outlet through which said fluid stream is removed from said fluid flow passage, wherein said preselected distance of separation between said thermal mass and the facing of said first or second surfaces of said thermoelectric module is effective, when said temperature differential is formed, to permit the particles in the fluid stream to undergo thermophoretic movement and collect on said thermal mass or said first surface of said thermoelectric module and be removed from suspension in the fluid stream; and a pump in fluid flow communication with said fluid flow passage for inducing flow of said fluid stream.

45. The thermal particle precipitator of claim 44, including a sensor associated with said first surface of the thermoelectric module for analyzing said collected particles.

46. The thermal particle precipitator of claim 45, wherein said sensor is selected from the group consisting of electrochemical, optical acoustic, thermal and biological sensors.

47. The thermal particle precipitator of claim 44, including a microchip comprising a biological sensor associated with said first surface of the thermoelectric module for analyzing said collected particles.

48. A thermal particle precipitator for removing and collecting particles from a fluid stream, said precipitator comprising:
 a thermoelectric module mounted for rotative movement and having first and second surfaces and operable upon application of a direct current to provide cooling of said first surface and heating of said second surface;
 a thermal mass spaced apart in a facing relationship to said first or second surface of said thermoelectric module by a preselected distance of separation sufficient to form a temperature differential between said thermal mass and said first or second surface of said thermoelectric module when said thermoelectric module is operated to provide cooling of said first surface and heating of said second surface; and
 a fluid flow passage formed in the close spacing between said thermal mass and the facing one of said first or second surfaces of said thermoelectric module and having an inlet through which a fluid stream containing suspended particles is introduced into said fluid flow passage for travel along and between said thermal mass and the facing one of said first or second surfaces of said thermoelectric module and an outlet through which said fluid stream is removed from said fluid flow passage, wherein said preselected distance of separation between said thermal mass and the facing of said first or second surfaces of said thermoelectric module is effective, when said temperature differential is formed, to permit the particles in the fluid stream to undergo thermophoretic movement and collect on said thermal mass or said first surface of said thermoelectric module and be removed in the fluid stream.

49. The thermal particle precipitator of claim 48, including a sensor associated with said first surface of the thermoelectric module for analyzing said collected particles.

50. The thermal particle precipitator of claim 49, wherein said sensor is selected from the group consisting of electrochemical, optical, acoustic, thermal and biological sensors.

51. The thermal particle precipitator of claim 48, including a microchip comprising a biological sensor associated with said first surface of the thermoelectric module for analyzing said collected particles.

52. A thermal particle precipitator for removing and collecting particles from a fluid stream, said precipitator comprising:
 a thermoelectric module having first and second surfaces and operable upon application of a direct current to provide cooling of said first surface and heating of said second surface;
 a thermal mass spaced apart in a facing relationship to said first or second surface of said thermoelectric module by a preselected distance of separation sufficient to form a temperature differential between said thermal mass and said first or second surface of said thermoelectric module when said thermoelectric module is operated to provide cooling of said first surface and heating of said second surface; and
 a fluid flow passage formed in the spacing between said thermal mass and the facing one of said first or second surfaces of said thermoelectric module and having an inlet through which a fluid stream containing suspended particles is introduced into said fluid flow passage for travel along and between said thermal mass and the facing one of said first or second surfaces of said thermoelectric module and an outlet through which said fluid stream is removed from said fluid flow passage, wherein said preselected distance of separation between said thermal mass and the facing of said first or second surfaces of said thermoelectric module is effective, when said temperature differential is formed, to permit the particles in the fluid stream to undergo thermophoretic movement and collect on said thermal mass or said first surface of said thermoelectric module and be removed from suspension in the fluid stream,
 wherein said first surface of the thermoelectric module includes a removable or embedded particle collection substrate and wherein said collection substrate includes a sensor.

53. The thermal particle precipitator of claim 52, including a sensor associated with said first of the thermoelectric module for analyzing said collected particles.

54. The thermal particle precipitator of claim 53, said sensor is selected from the group consisting of electrochemical, optical, acoustic, thermal and biological sensors.

55. The thermal particle precipitator of claim 52, including a microchip comprising a biological sensor associated with said first surface of the thermoelectric module for analyzing said collected particles.

56. The thermal particle precipitator of claim 52, wherein said thermal mass is a heat source.

57. The thermal particle precipitator of claim 56, wherein said heat source is another thermoelectric module.

58. The thermal particle precipitator of claim 56, wherein said heat source is ambient air and the facing one of said first or second surfaces of thermoelectric module is said first surface.

59. The thermal particle precipitator of claim 52, wherein said thermal mass is a heat sink comprising a surface having a lower temperature than the facing one of said first or second surfaces of said thermoelectric module.

60. The thermal particle precipitator of claim 52, including a heat sink attached to said second surface of said thermoelectric module to draw heat from said second surface of said thermoelectric module.

61. A thermal particle precipitator for removing and collecting particles from a fluid stream, said precipitator comprising:
 a thermoelectric module having first and second surfaces and operable upon application of a direct current to provide cooling of said first surface and heating of said second surface;
 a thermal mass having a first portion spaced apart in a facing relationship to said first surface of said thermoelectric module by a preselected distance of separation sufficient to form a temperature differential between said thermal mass and said first surface of said thermoelectric module when said thermoelectric module is operated to provide cooling of said first surface and heating of said second surface, wherein said thermal mass is in thermal communication with said second surface of the thermoelectric module to transfer heat from said second surface of the thermoelectric module to the first portion of the thermal mass; and a fluid flow passage formed in the close spacing between said first portion of the thermal mass and the first surface of said thermoelectric module and having an inlet through which a fluid stream containing suspended particles is introduced into said fluid flow passage for travel along and between said first portion of the thermal mass and the first surface of said thermoelectric module and an outlet through which said fluid stream is removed from said fluid flow passage, wherein said preselected distance of separation between said thermal mass and the first surface of said thermoelectric module is effective, when said temperature differential is formed, to permit the particles in the fluid stream to undergo thermophoretic movement and collect on said first surface of said thermoelectric module and be removed from suspension in the fluid stream.

62. The thermal particle precipitator of claim 61, including a sensor associated with said first surface of the thermoelectric module for analyzing said collected particles.

63. The thermal particle precipitator of claim 62, wherein said sensor is selected from the group consisting of electrochemical, optical acoustic, thermal and biological sensors.

64. The thermal particle precipitator of claim 61, including a microchip comprising a biological sensor associated with said first surface of the thermoelectric module for analyzing said collected particles.

65. A thermal particle precipitator for removing and collecting particles from a fluid stream, said precipitator comprising:

a thermoelectric module having first and second surfaces and operable upon application of a direct current to provide cooling of said first surface and heating of said second surface;

a thermal mass spaced apart in a facing relationship to said first or second surface of said thermoelectric module by a preselected distance of separation sufficient to form a temperature differential between said thermal mass and said first or second surface of said thermoelectric module when said thermoelectric module is operated to provide cooling of said first surface and heating of said second surface;

a battery operatively coupled with said thermoelectric module to provide a direct current thereto, wherein said battery is positioned in thermal communication with said thermal mass to transfer heat thereto; and a fluid flow passage formed in the spacing between said thermal mass and the facing one of said first or second surfaces of said thermoelectric module and having an inlet through which a fluid stream containing suspended particles is introduced into said fluid flow passage for travel along and between said thermal mass and the facing one of said first or second surfaces of said thermoelectric module and an outlet through which said fluid stream is removed from said fluid flow passage, wherein said preselected distance of separation between said thermal mass and the facing of said first or second surfaces of said thermoelectric module is effective, when said temperature differential is formed, to permit the particles in the fluid stream to undergo thermophoretic movement and collect on said thermal mass or said first surface of said thermoelectric module and be removed from suspension in the fluid stream.

66. The thermal precipitator of claim 65, including a sensor associated with said first surface of the thermoelectric module for analyzing said collected particles.

67. The thermal particle precipitator of claim 66, wherein said sensor is selected from the group consisting of electrochemical, optical, acoustic, thermal and biological sensors.

68. The thermal particle precipitator of claim 65, including a microchip comprising a biological sensor associated with said first surface of the thermoelectric module for analyzing said collected particles.

69. A method for removing and collecting particles from a fluid stream comprising: creating a temperature gradient between a thermoelectric module and a thermal mass; flowing a fluid stream containing suspended particles along a flow passage through said temperature gradient to cause said suspended particles to undergo thermophoretic movement in the direction of a cooler end of the temperature gradient; collecting at least a portion of said suspended particles on a surface of said thermoelectric module or said thermal mass as a result of said thermophoretic movement; heating said surface of the thermoelectric module or said thermal mass to cause vapors to be released from said suspended particles which have collect on said surface; and then flowing a carrier fluid through said flow passage to collect said release vapors.

70. The method of claim 69, including analyzing said vapors which have been collected in said carrier fluid.

* * * * *